United States Patent [19]
Horan

[11] Patent Number: 5,363,958
[45] Date of Patent: Nov. 15, 1994

[54] BLADE ARMING CARTRIDGE

[75] Inventor: Robert T. Horan, Northridge, Calif.

[73] Assignee: Devon Industries, Inc., Chatsworth, Calif.

[21] Appl. No.: 48,463

[22] Filed: Apr. 14, 1993

[51] Int. Cl.⁵ .................................. B65D 83/10
[52] U.S. Cl. .................... 206/356; 206/493; 30/339
[58] Field of Search ............... 206/352, 354, 355, 356, 206/357, 358, 359, 360, 821, 493, 349; 30/40.2, 40, 123, 339; 29/239, 178

[56] References Cited

U.S. PATENT DOCUMENTS

| | | | |
|---|---|---|---|
| 1,986,230 | 1/1935 | Talbot | 206/354 |
| 2,581,332 | 1/1952 | Testi | 206/358 |
| 4,180,162 | 12/1979 | Magney | 206/356 X |
| 4,397,389 | 8/1983 | Findeisen | 206/821 X |
| 4,746,016 | 5/1988 | Pollak et al. | 206/356 |
| 5,088,173 | 2/1992 | Kromer et al. | 206/355 X |

Primary Examiner—Paul T. Sewell
Assistant Examiner—Jacob K. Ackun, Jr.
Attorney, Agent, or Firm—Poms, Smith, Lande & Rose

[57] ABSTRACT

A cartridge for an implement is described for holding the implement and for permitting access by a tool to which the implement is to be mounted, the cartridge comprising a housing and a releasable block for inhibiting the implement from moving in a rearward direction out of the housing. In a specific embodiment, the cartridge is a scalpel arming cartridge for holding a scalpel blade wherein the releasable block is a rearward releasable block for inhibiting the blade from moving in a rearward direction and out of the housing.

13 Claims, 3 Drawing Sheets

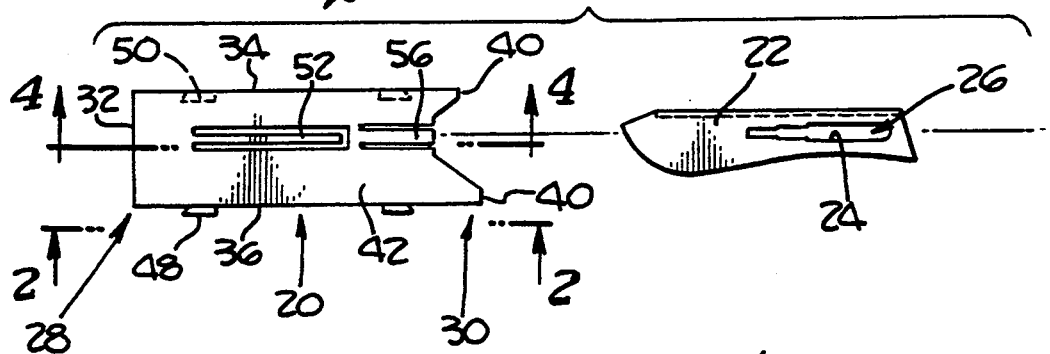
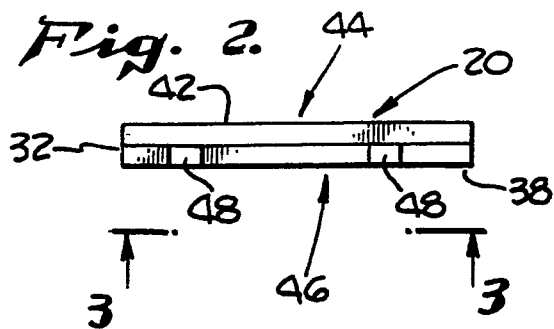
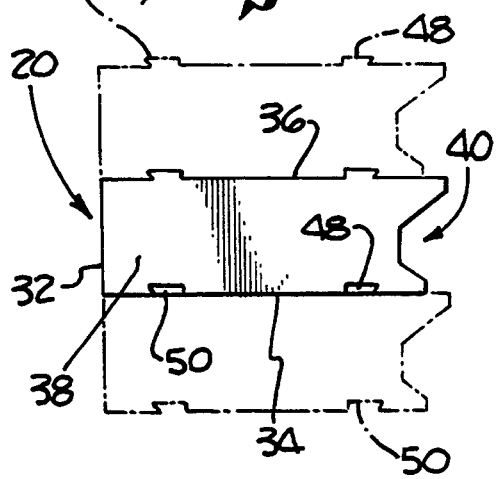
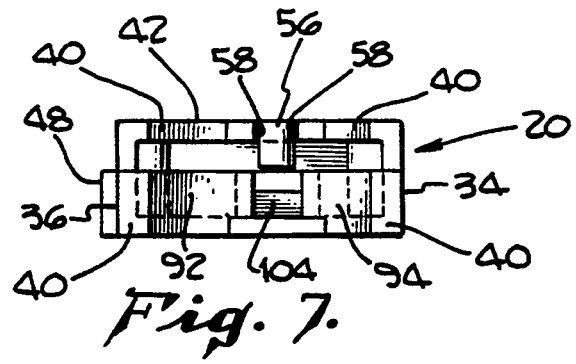
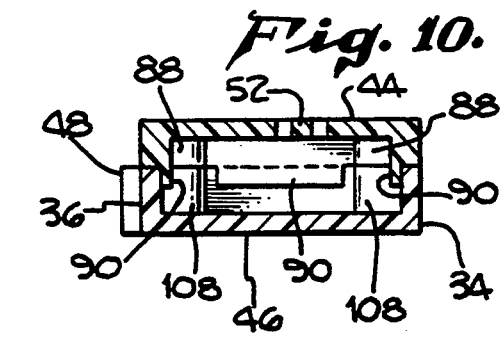
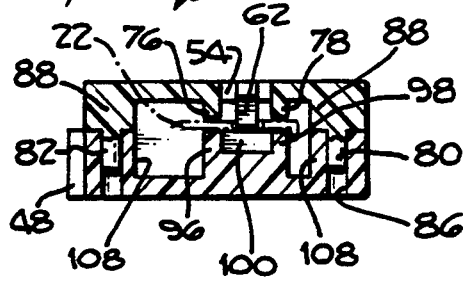
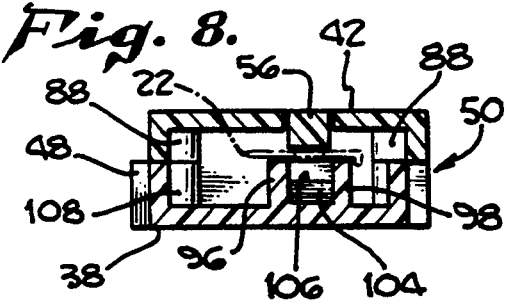

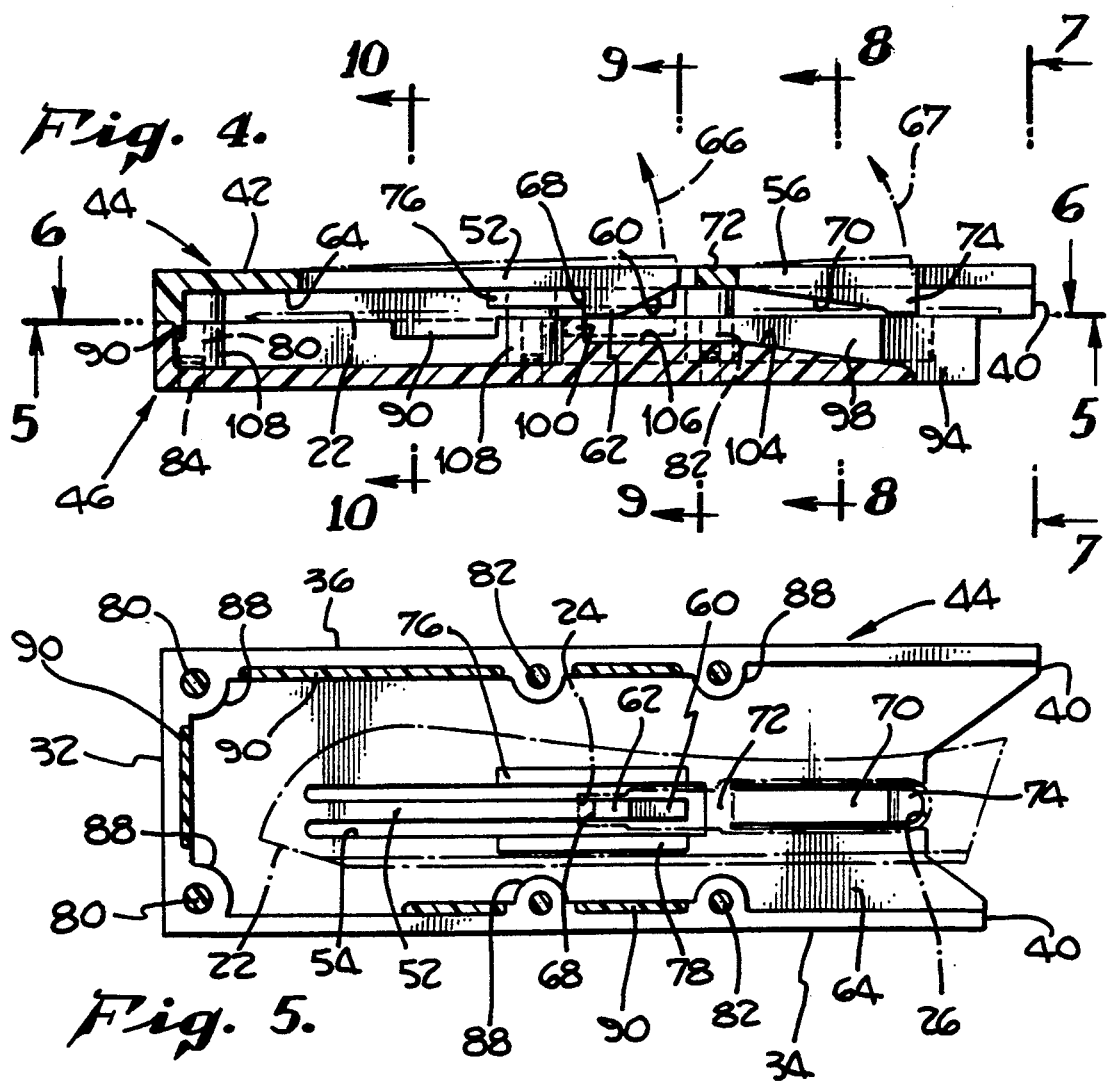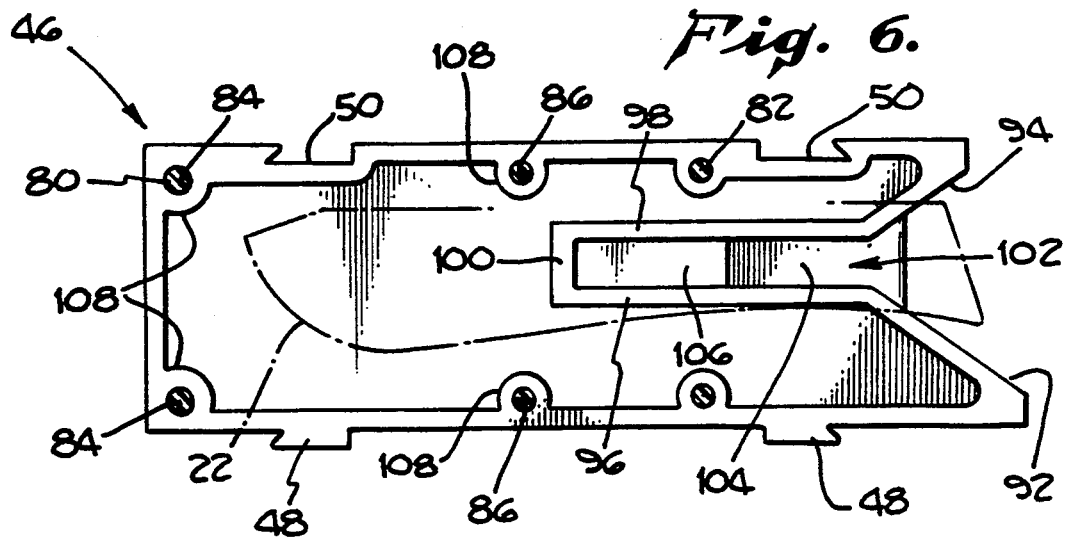

BLADE ARMING CARTRIDGE

BACKGROUND OF THE INVENTION

1. Field of the Invention

The present invention relates to housings for tool implements such as blades which can also accept the tool for mounting the implement on the tool, and, in one embodiment thereof, to a blade arming cartridge for housing a blade and accepting a handle for mounting the blade on the handle.

2. Related Art

With advancements in technology, many tools and instruments are reusable whereby a handle or other sturdy element is used numerous times in conjunction with a disposable or limited-life implement such as a blade or other working element. For example, scalpels often have a sturdy handle and a blade portion removably mounted on the handle for use during a given procedure. After the blade has been used, the blade is removed and discarded, after which the handle is sterilized and made ready for further use by mounting a new blade. In many instances, new blades are packaged in individual sterile packages formed by two sheets of paper or aluminum foil sealing the blade between them, much like finger bandages are packed. When the blade is to be mounted on the its handle, one paper or aluminum foil layer is folded back to expose the rearward or mounting portion of the blade. The package is then grasped so as to press the sides of the blade between the thumb and forefinger while the handle is inserted into the opening of the blade. While the blade should be held so that the cutting edge points away from the user, the potential for injury still exists. Slipping of the blade within the paper or aluminum foil, in conjunction with the force required to properly install the blade on the handle, may push the blade through the cover and cause injury. Nothing prevents the blade from moving relative to its envelope and nothing prevents the blade from puncturing the cover. Therefore, individuals are subject to injury while installing the blade on the handle.

Storage of new scalpel blades in paper or aluminum foil packages presents a significant possibility of injury. Individual scalpel packages can fall out of the box in which they are stored and may fall under foot or onto a countertop unnoticed. Ordinary movement around a laboratory or operating room may result in inadvertent cuts or puncture wounds through the cover. Therefore, normal storage of conventional replacement scalpel blades presents a possibility of injury.

Similar problems may arise with respect to other disposable implements to be mounted on tools. The implement may not be adequately housed or protected during normal storage and may not hold the implement sufficiently stable while the implement is being mounted on its handle or other implement.

There is a need, therefore, for a cartridge or implement housing for safely and reliably containing and protecting the implement, such as a scalpel blade. There is also a need for a cartridge which can safely and reliably accept the mounting portion of the handle or other tool portion for mounting the blade or implement on the tool.

It is an object, therefore, of the present invention to provide a cartridge or other housing for an implement such as a scalpel blade for holding and protecting the implement while at the same time minimizing the possibility that the blade may puncture the housing during normal storage or while the blade is being mounted on the tool.

It is a further object of the present invention to provide a blade cartridge which easily accepts the blade mounting portion of the scalpel handle to mount the blade on the handle while minimizing the possibility that the blade may puncture or pass through the sides of the cartridge.

It is an additional object of the present invention to provide a cartridge which holds the blade substantially stationary in all three mutually perpendicular directions, so that the blade cannot move forward or backward, sideways or up and down within the housing during normal storage.

It is a still further object of the present invention to provide a cartridge which is easy to assemble with the blade inside.

It is another object of the present invention to provide a scalpel blade cartridge which is rigid for protecting the blade and for preventing puncture of the walls of the cartridge.

It is an additional object of the present invention to provide a blade cartridge whereby the cartridge is stackable with similar cartridges containing the same or other blades for storage and for easy access for mounting the blade on a handle.

These and other objects are provided according to the present invention to be described more fully below.

SUMMARY OF THE INVENTION

In accordance with the present invention, an implement housing for holding an implement is provided which minimizes the possibility of movement of the implement within the housing during ordinary storage and which minimizes the possibility that the implement breaches the walls of the housing during storage or when the implement is being mounted on its associated tool. The housing additionally protects the implement from external impact. The present invention also provides a cartridge which can easily accept a tool for mounting the implement on the tool and allowing withdrawal of the implement from the housing for normal use. Therefore, in accordance with the present invention, a housing is provided for enclosing the implement. The housing includes a block for inhibiting the implement from moving longitudinally, such as in a rearward direction relative to the housing to prevent removal of the implement from the housing. A block may also inhibit the implement from moving forward. The block may be releasable, such as by a tool, so that the tool can be installed on the tool and the tool can then remove the implement from the housing.

In one form of the invention, the housing includes a block for inhibiting the blade from moving in a forward direction and a block for inhibiting the blade from moving in the rearward direction so that the implement, such as a blade, is fixed in both directions until a suitable tool is inserted in the housing to allow removal of the implement.

In one embodiment of the invention, the housing is a scalpel arming cartridge for holding a scalpel blade. The scalpel blade has a mounting wall defining an opening for mounting the blade onto the scalpel handle and for permitting access by a scalpel handle to mount the blade. The cartridge includes a housing for enclosing a substantial portion of the scalpel blade and a wall in the housing defining an opening for accepting a scalpel handle. A forward releasable block inhibits the blade from moving in a forward direction away from the wall of the housing. A rearward releasable block inhibits the blade from moving in a rearward direction toward the wall of the housing. The blocks are releasable after a scalpel blade is at least partially mounted onto a handle and can be safely removed from the cartridge.

In a further preferred form of the invention, the cartridge includes a ramp for guiding a part of the scalpel handle into the cartridge so that the scalpel blade automatically mounts on the handle as the handle is being inserted into the cartridge. Movement of the handle preferably releases the blocks and allows removal of the blade from the cartridge.

The forward releasable block is preferably cantilevered to a mounting position on the housing, and the free end of the forward releasable block is preferably a sufficient distance from the mounting position to provide a resiliency sufficient to capture the blade and hold the blade while a scalpel handle is separated from the housing and to release the blade when a scalpel handle is inserted into the housing. In this manner, the scalpel handle provides the releasing function, preferably only after the scalpel blade has been suitably mounted on the handle, without which the blade cannot be removed from the housing.

In a further preferred form of the invention, the cartridge preferably includes means for mounting one cartridge to another, thereby permitting stacking or other acceptable storage or form of presentation.

The present invention will be further understood in conjunction with consideration of the drawings, a brief description of which is provided below, along with the detailed description of the preferred embodiments.

BRIEF DESCRIPTION OF THE DRAWINGS

FIG. 1 is an exploded and top plan view of an implement housing and an implement to be stored in the housing for later removal by a suitable tool according to the present invention.

FIG. 2 is a side elevation view of the housing of FIG. 1 taken along lines 2—2.

FIG. 3 is a bottom plan view of the housing according to the present invention showing an arrangement for interlocking multiple housings for stacking or other storage or presentation arrangement.

FIG. 4 is a longitudinal side section of the housing of FIG. 1 taken along lines 4—4 and showing an implement such as a scalpel blade in its environment within the housing.

FIG. 5 is a longitudinal section through the top of the housing showing the inside surface of the top-half of the housing taken along lines 5—5 of FIG. 4.

FIG. 6 is a longitudinal section of the bottom showing the inside surface of the bottom portion of the housing taken along lines 6—6 of FIG. 4.

FIG. 7 is a rearward elevation view of the housing taken along lines 7—7 of FIG. 4.

FIG. 8 is a transverse rearward section of the housing taken along lines 8—8 of FIG. 4.

FIG. 9 is rearward transverse section of the housing of FIG. 4 taken along lines 9—9.

FIG. 10 is a forward transverse cross-section of the housing of FIG. 4 taken along lines 10—10.

DETAILED DESCRIPTION OF THE PREFERRED EMBODIMENTS

Figure 11:
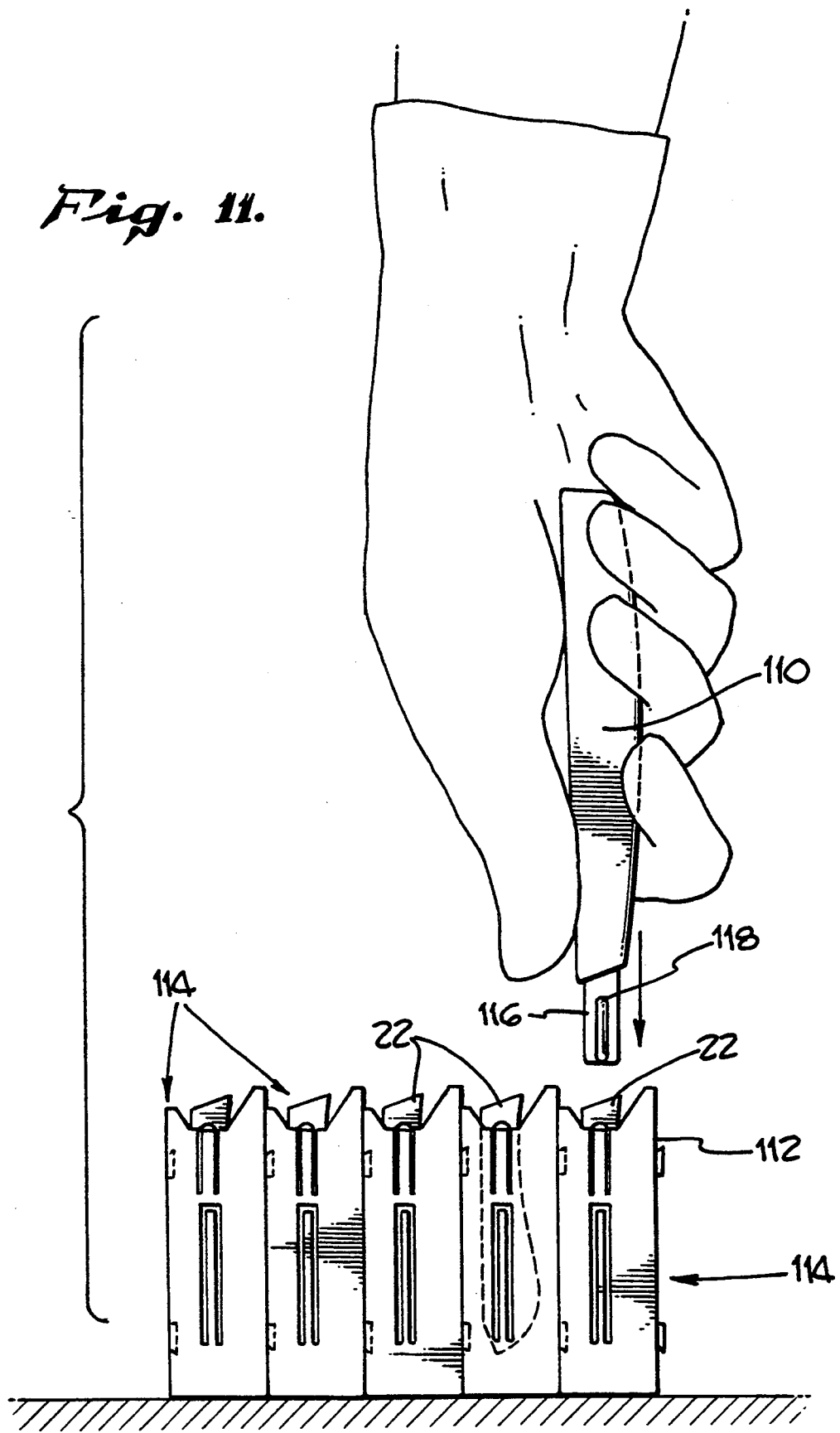
FIG. 11 shows a top plan view of a series of scalpel cartridges containing scalpel blades and depicting a scalpel handle about to be inserted into a cartridge for mounting a blade on the scalpel handle.

In accordance the present invention, a housing for holding an implement is provided which protects the implement and minimizes the possibility of breaching the housing so that the implement is no longer protected or so that the implement is no longer fully enclosed. In accordance with the present invention, a housing, for example a scalpel arming cartridge 20 (FIG. 1), is provided for holding an implement such as a scalpel blade 22 or other disposable implement, to be placed on a handle or other tool. In the preferred embodiment disclosed herein, the scalpel blade is a conventional blade having a mounting wall 24 defining an opening 26 for mounting the blade onto a scalpel handle (depicted in FIG. 11). While the implement described herein in the preferred embodiment is a scalpel blade (FIG. 1) it should be understood that other implements may be accommodated by a housing or cartridge having the properties or characteristics of the present invention. The beneficial features of the present invention can be incorporated in a manner which will be apparent to those skilled in the art upon reviewing the drawings and description herein to accommodate other implements. The specific configuration of the cartridge and its walls, and the like, can be modified within the scope of the invention to accommodate different forms of implements. The following discussion of the housing and its use will be made in conjunction with the specific embodiment of a scalpel blade and its mounting on a scalpel handle.

In the preferred embodiment, the housing 20 substantially encloses the blade. The housing includes a forward or distal end 28 and a rearward or proximal end 30. The scalpel blade cartridge is preferably closed at the distal face 32, the right-side wall 34 and at the left-side wall 36 to substantially fully enclose the distal and side edges of the scalpel blade. The bottom side 38 (FIG. 3) is continuous to substantially fully close the bottom portion of the cartridge. The proximal end 30 of the cartridge preferably includes a wall 40 (FIGS. 1 and 7) for permitting access by the distal tip of a scalpel handle to the interior of the cartridge for mounting the blade onto the scalpel handle. While the wall 40 may take a number of configurations depending on the shape of the scalpel blade, the side portions of the wall 40, near the sides 34 and 36, extend sufficiently in the proximal direction to adequately protect the exposed proximal end of the scalpel blade while the blade is in the cartridge. In the preferred embodiment, a line connecting the proximal ends of each of the right-side wall 34 and left-side wall 36 passes proximal of the proximal-most extent of the blade when the blade is properly positioned within the cartridge, or at least in the area of the proximal-most extent of the blade. Additionally, there is preferably sufficient clearance provided by the wall 40 to permit complete access by the blade mounting portion of the scalpel handle to the cartridge and the blade therein. A top wall 42 substantially closes the remainder of the housing.

In the preferred embodiment, the housing is formed from two discrete elements, namely a top-half 44 (FIG. 2) and a bottom-half 46, for ease of manufacture and assembly. The internal configuration of the top-half and the bottom-half will be described more fully below. Externally, the bottom-half 46 includes engagement elements such as a pair of mirror imaged but non-symmetrical, trapezoidal tongues 48 extending the thickness of the bottom-half. The sides of the tongues facing toward each other extend substantially perpendicular to the left-side wall 36 and the surfaces facing away from each other are slanted relative to the left-side wall 36. A pair of corresponding grooves 50 (FIG. 1 ) are formed in the right-side wall 34 to accept mating tongues from an adjacent cartridge, substantially as shown in FIG. 3. The tongues and grooves are preferably oriented on the housings so that the housings can be joined in only one relative orientation, e.g., so that the openings to the housings all point in the same direction. One way to accomplish unidirectionality is to configure the tongues and grooves so that the slanted parts thereof all face in the same direction. The tongues and grooves provide the ability to stack multiple cartridges together for ease of storage, packaging, shipping and presentation for use. Stacked cartridges provide an organized arrangement for presenting scalpel blades for installation, such as depicted in FIG. 11. Stacked cartridges also provide a convenient mechanism by which various combinations of scalpel blades can be presented for use at one time. For example, two of every three cartridges may contain a No. 10 scalpel blade and the third may contain a No. 15 scalpel blade, since, on the average, twice as many No. 10 blades may be used as No. 15 blades. Other arrangements are also possible. Groups of three or more may be assembled in a stacked arrangement and placed in wrappers for storage and shipping to maintain the sterile condition of the blades until the wrapper is opened.

In the preferred embodiment, the cartridge is formed from a rigid, clear plastic to minimize the possibility of breach of the wall of the cartridge by outside impact or by force applied to the scalpel blade. Rigidity protects the blade from impact as well as protects users from the sharp blade through inadvertence. The cartridge is preferably formed from clear styrene.

A releasable block/barrier, retainer, latch or other mechanism for inhibiting the blade from moving in a rearward or proximal direction relative to the cartridge keeps the blade within the cartridge until such time as a scalpel handle mounts the blade thereon and releases the blade from the cartridge. Preferably, mounting of the blade on the handle occurs to a sufficient degree before the blade is released so that the blade does not disengage from the handle after the blade is released from the cartridge. Use of a releasable block, in conjunction with a rigid cartridge provides a safe and reliable storage cartridge and installation mechanism which minimizes injury to staff by the scalpel blade, minimizes infection of a patient by a staff member who may have been injured by an unprotected blade, and minimizes the possibility of staff absences due to injury during use of the scalpel blade, where the absence may be required because of an open wound.

In the preferred embodiment shown in FIG. 1, the releasable block takes the form of a first releasable latch 52 cantilevered from a relatively distal portion of the top wall 42 and extends proximally along the approximate center of the top wall 42 to a point proximal of the middle of the cartridge. The first releasable latch 52 rests in a groove 54 in the top wall so that the latch 52 can flex resiliently in the groove 54 and out of the plane of the top wall 42. As will be discussed more fully below, flexing of the first releasable latch 52 upward relative to the top wall 42 permits release of the scalpel blade 22 and rearward movement. An interior portion of the latch 52 engages the distal edge of the blade mounting wall 24 to prevent the scalpel from being removed from the cartridge proximally, as discussed more fully below.

Ingress or forward movement of the scalpel blade relative to the cartridge may be limited or prevented by a number of mechanisms. For example, a stopping wall may be provided adjacent the distal tip of the scalpel blade to prevent the blade from moving forward. However, a wall contacting the sharpened edge of the scalpel blade may dull or otherwise adversely affect the condition of the blade. In a preferred embodiment of the present invention, a second releasable latch 56 is cantilevered from a portion of the top surface 42 proximal of the groove 54 and rests in grooves 58 (FIG. 7). The second latch preferably extends to the proximal-most portion of the middle of the top wall 42. Preferably, the first and second releasable latches extend along a common central axis. The second releasable latch 56 is movable upwardly relative to the top wall 42. As shown in FIG. 1, the width of the second releasable latch 56 is preferably larger than the width of the first latch 52. The second latch is therefore stiffer or less flexible than the first latch 52. The second latch 56 is also shorter than the first latch, also making the second latch less flexible relative to the first releasable latch. The proximal-most end surface of the second releasable latch engages the proximal-most portion of the blade mounting wall 24 to inhibit the blade from moving in a forward direction away from the wall 40 and closer to the distal face 32. Therefore, with the first and second releasable latches, the scalpel blade is held longitudinally fixed during storage and until a scalpel handle is properly inserted into the scalpel blade cartridge. Moreover, with the configurations of the releasable latches and their positioning in the mounting wall 24 of the blade, the blade is also held substantially stationary in the lateral direction.

Considering the first releasable latch 52 in more detail (FIGS. 4, 5 and 7-10), the first releasable latch 52 includes a proximally facing cam surface 60 sloping downwardly or interiorly from the proximal end of the releasable latch to form a tang 62 on the lower proximal portion of the first latch. The cam surface 60 terminates at the bottom of the tang. The cam surface extends approximately from the level of the bottom surface 44 of the top wall 42 down to a level approximately at the intersection between the top-half and the bottom-half of the cartridge. The cam surface 60 is contacted by the tang on the scalpel handle, well known to those skilled in the art, and is cammed upwardly as the scalpel handle is inserted into the cartridge, thereby lifting the first releasable latch 52 in a direction, designated by arrow 66, outwardly of the cartridge. The tang 62 includes a substantially straight, non-curved blocking wall 68 for engaging the corresponding surface in the scalpel blade for preventing movement of the blade proximally while the first latch is in the position shown in FIG. 4. The width of the first latch is sufficiently narrow to allow the latch to easily engage the distal-most portion of the blade mounting wall 24. The width is preferably great enough to reliably engage the mounting wall 24 and contribute to holding the blade substantially laterally stationary. The tang 60 preferably is sized sufficiently to avoid breakage or chipping of the material under normal conditions of use.

The second releasable latch includes its own camming surface 70 sloping inwardly and proximally from the bottom surface of a web 72, in the top surface 42 separating the first and second releasable latches and forming the part of the top surface from which the second releasable latch is cantilevered. The cam surface 70 extends inwardly approximately from a level of the bottom surface 64 substantially to a tang 74, at which it curves downwardly to the bottom surface of the tang 74, as shown in FIG. 4. The bottom of the tang 74 is approximately at the same level as the bottom of the tang 62 on the first releasable latch. Preferably, the proximal-most surface on the tang 74 is rounded into the shape of a semi-circle, in plan view, as shown in FIG. 5, for that portion of the tang which extends below the bottom surface 64. The semi-circular surface conforms to the rounded surface on the proximal-most portion of the mounting wall 24 in the scalpel blade. That portion of the second latch at the proximal end and at the level of the top wall 42 may be squared off, as shown in the top plan view shown in FIG. 1.

Considering the top-half 44 of the cartridge in more detail, particularly with respect to FIG. 5, the top-half 44 includes a pair of ridges 76 and 78 to maintain the blade in a plane immediately adjacent a plane defined by a junction plane between the top-half 44 and the bottom-half 46 of the cartridge. As can be seen in FIG. 4, the blade 22 is positioned approximately above the junction plane. The two ridges 76 and 78 (FIGS. 4, 5 and 9) extend inwardly relative to the interior of the cartridge from the inside surface 64 of the top-half of the cartridge. Each ridge is contiguous with the groove 54. The ridges are spaced apart a sufficient distance to accommodate and guide the tang on a scalpel handle as the tang is inserted into the opening 26 in the scalpel blade. The ridges are preferably thick enough to avoid breaking or cracking when the scalpel handle is inserted into the cartridge. The ridges are preferably long enough to extend distally beyond the blocking wall 68 in the first releasable latch 52 so as to continue guiding the tang on the scalpel handle as the scalpel handle is inserted into the cartridge.

The top-half 44 includes two large pins 80 and four small pins 82, preferably, to engage corresponding holes 84 and 86, respectively, in the bottom half 46 (FIG. 6). By way of example, the large pins 80 may be 60 mils in diameter, the small pins may be 40 mils in diameter, and the holes 84 and 86 are preferably sized so as to create a permanent press fit through interference with the pins. The holes may be sized two to three mils smaller in diameter to achieve the press fit. Alternatively, or additionally, the two-halves of the cartridge may be ultrasonically welded together or otherwise bonded or sealed. Each pin preferably is centered on a boss 88 for structural integrity.

The side walls and the distal face 32 include a plurality of flanges 90 extending between the bosses 88. The flanges 90 assist in mating the two-halves of the cartridge and insure a positive junction between the two-halves.

In the preferred embodiment, the bottom-half 46 of the cartridge provides the structure for stacking the cartridges together through the tongues 48 and grooves 50, and also provides a guide for the distal end of the scalpel handle as the scalpel handle is being inserted into the cartridge for mounting the scalpel blade. The proximal portion of the bottom-half 46 includes a left guide wall 92 and a right guide wall 94 for laterally guiding the distal end of the scalpel handle into the cartridge. The left and right guide walls 92 and 94 form surfaces at approximately 35 degrees relative to the longitudinal axis of the cartridge. The wall 40 in the top-half conforms to the same angles as can be seen in FIG. 1. The left and right guide walls 92 and 94 form part of the wall 40 defining the opening to the cartridge discussed above.

The left and right guide walls terminate at parallel spaced apart left and right inlet walls 96 and 98, which in turn terminate at an end wall 100 across the distal end of the inlet 102. The guide walls 92, 94, inlet walls 96, 98, and the end wall 100 extend upwardly from the inside bottom surface of the cartridge to a level which is co-planar with the rest of the bottom-half of the cartridge. The top surfaces of the walls 92–100 provide a support surface for the scalpel blade. Additionally, the distal portion of the left and right inlet walls and the end wall 100 serve as a base against which the adjacent portion of the scalpel blade is sandwiched by the opposite surfaces of the ridges 76 and 78 extending downwardly from the upper-half of the cartridge.

The bottom of the inlet 102 is closed by a proximal ramp portion 104 terminating in a non-ramped, horizontal sliding surface 106. The ramp portion 104 preferably terminates at approximately the same longitudinal position on the bottom-half as the cam surface 70 terminates at the web 72 on the upper-half of the cartridge. As can be seen in FIG. 4, the ramp portion 104 and the cam surface 70 define a slanted groove for accepting and guiding the distal portion of the scalpel handle as it is being inserted into the cartridge so that the tang on the scalpel handle can slide into the opening 26 in the scalpel blade and begin to engage the wall 24 in the scalpel blade.

The bottom-half 46 of the cartridge also includes bosses 108 in which the holes 84 and 86 are formed. In the preferred embodiment, the holes are formed completely through the bottom-half of the cartridge.

The latches and the walls 92–100 are preferably formed so that the blade is held stationary, and so that any possible movement of the blade relative to the housing would not result in any contact between the sharpened edge of the blade and any part of the housing. While contact between the housing and other edges of the blade may be acceptable, movement of the blade other than out of the housing in normal use is not preferred. While the latches have been described as being separate elements, the two latches can be formed from a single element, and the respective latch elements may extend from a variety of positions on the housing to engage respective portions of the mounting wall 24 of the blade for stabilizing the blade. However, it is preferred to have that latch which inhibits rearward blade movement be released before the latch, if any, which inhibits forward blade movement, so that proper mounting of the blade on the handle can be achieved before full release of the blade.

The blade is preferably positioned in a plane parallel to the bottom side 38 and the top wall 42 so that the distal tip of the scalpel handle can approach the mounting wall 24 at an angle on the ramp 104. Other configurations are possible for providing an angle of attack for the scalpel handle, but a co-planar blade permits an easier housing design.

In the context of surgical instruments such a breakable block is not preferred. Breaking of a block, such as a plastic block, would probably create chips or other undesirable particulates unsuitable in surgery and other medical applications.

The cartridge and blade may be assembled as would be apparent to one skilled in the art. For example, the bottom-half may be stabilized in a pre-determined position, such as by the holes 84 and 86, and the blade positioned on the top surfaces of the walls 92-100. While maintaining the blade and the bottom-half stationary, the top-half may then be brought down over the blade, sandwiching the blade between the ridges 76 and 78 and the walls 92-100 and so that the tangs 60 and 74 pass into the scalpel blade opening 26. The pins 80 and 82 pass into and frictionally engage the holes 84 and 86 to provide an interference fit. The scalpel cartridge is thus easy to assemble, and also may lend itself to easy automated assembly. Numerous filled cartridges can then be stacked using the tongues 48 and grooves 50 according to any desired number and configuration.

The scalpel arming cartridge according to the present invention provides a rigid housing for a scalpel blade which is visible through the walls of the cartridge. In the preferred embodiment, the scalpel blade is held in position longitudinally so that the blade does not move forward or distally and does not move rearwardly or proximally until such time as a scalpel handle is sufficiently inserted into the cartridge and engages the scalpel blade and the blade is mounted on the scalpel handle. The cartridge is easy to handle and serves to protect the blade from external impact, and to minimize injury to staff, minimize infection of a patient by a staff member resulting from an injury to a staff member by an exposed scalpel blade and is more reliable. The cartridge holds the blade while still allowing removal after appropriate manipulation with a scalpel handle once the blade is mounted on the handle. The cartridges are stackable and may contain different blade sizes according to need or common usage. Stacking the cartridges provides neatness and ease of handling, storage and shipment.

Considering now the method of mounting a scalpel blade on a scalpel handle using the cartridge of the present invention, the user may grasp the scalpel handle 110 (FIG. 11) and advance the scalpel handle toward a cartridge 112 in a stack of cartridges 114. The handle includes a blade support 116 and a T-shaped tang 118 extending longitudinally along the surface of the blade support. The blade support 116 first contacts either or both of the left and right guide walls 92 and 94 until the blade support passes into the inlet 102 between the left and right inlet walls 96 and 98, respectively. It should be noted that the width of the blade support 116 is enlarged for purposes of illustration. As the blade support passes along the inlet 102, the bottom of the blade support rides up the ramp portion 104 until such time as the tang 118 on the blade support passes into the opening 26 in the blade. The ramp portion 104 extends upwardly toward the blade a sufficient distance to allow the tang to pass through the opening so that the top of the tang extends above the blade. In the preferred embodiment, the ramp extends sufficiently high so that the top of the tang is positioned above the blade, namely between the blade and the bottom surface 64 of the top half of the cartridge, as the blade support continues to pass along the horizontal sliding surface 106 and between the left and right inlet walls 96 and 98, respectively.

After the blade support 116 passes the transition between the ramp portion 104 and the horizontal sliding surface 106, the top distal portion of the tang 118 contacts the cam surface 60 on the first latch 52. Additionally, the leg of the T-shaped tang 118 passes between the narrow portions of the blade mounting wall 24. As the blade support 116 and tang 118 continue along the sliding surface 106, the top distal portion of the tang 118 cams the first latch 52 upward, in the direction depicted by arrow 66 (FIG. 4) by engaging the camming surface 60. It should be noted that arrows 66 and 67 (FIG. 4) merely indicate direction and do not depict the actual range of motion of the tangs. Camming of the first latch releases the latch from the opening 26 in the scalpel blade so that the scalpel blade can be moved proximally relative to the cartridge. As the blade support 116 and the tang 118 approach the end wall 100, the tang 62 on the first releasable latch will be fully raised out of the path of the scalpel blade when the scalpel blade is thereafter moved proximally relative to the cartridge. When the blade support 116 and tang 118 contact the end wall 100, the tang 118 will have been fully inserted into the opening 26 in the scalpel and will have moved distally relative to the scalpel blade itself the maximum distance permitted by the cartridge. It should be noted that forward or distal movement of the scalpel blade is prevented by the engagement of the second releasable latch 56 with the proximal end of the wall 24 in the scalpel. Therefore, the second releasable latch 56 permits complete engagement of the scalpel handle with the scalpel blade.

After the blade support 116 contacts the end wall 100, the scalpel handle can then be removed by following a reverse motion out of the inlet. The reverse motion brings the top proximal portion of the tang 118 into contact with the cam surface 70 on the second releasable latch 56 so that continued retraction of the scalpel handle from the cartridge cams the second releasable latch upwardly in the direction shown by arrow 67 so that the tang 74 on the latch 56 disengages from the opening in the scalpel blade, thereby permitting retraction of the blade from the cartridge. Since the blade is supported by the top surfaces of the walls 92-100, the blade stays in its original horizontal plane as it is being extracted from the cartridge. Because of the engagement of the tang 118 with the scalpel blade, the tang will eventually engage the proximal-most portion of the wall 24 of the scalpel blade and extract the blade from the cartridge upon continued retraction of the handle from the cartridge.

This method provides an easy and reliable procedure for mounting a scalpel blade on a handle, or other implement onto a tool, without requiring holding of the blade by the user or operation of any latches by the user to release the blade. The movement of the scalpel handle performs all engagement and unlatching functions, thereby minimizing any potential for injury or damage.

Although the present invention has been described in detail with reference only to the presently preferred embodiments, it will be appreciated by those of ordinary skill in the art that various modifications can be made without departing from the spirit of the invention. Accordingly, the invention is limited only by the following claims.

I claim:

1. A tool arming cartridge for holding a blade and facilitating mounting of the blade onto a tool handle having a blade supporting portion, the blade defining an opening adapted to receive the blade supporting portion, the tool arming cartridge comprising:

a housing defining an interior and an open longitudinal end;

blade engaging means, associated with the interior of the housing and movable between an engaged position and a disengaged position, for releasably engaging the opening in the blade; and biasing means for biasing the blade engaging means into the engaged position;

wherein the blade engaging means are reoriented from the engaged position to the disengaged position when the blade supporting portion of the tool handle is inserted into the open longitudinal end of the housing.

2. A tool arming cartridge as claimed in claim 1, wherein the opening in the blade defines first and second longitudinal ends and the blade engaging means comprises at least one block for engaging at least one of the longitudinal ends.

3. A tool arming cartridge as claimed in claim 2, wherein the blade engaging means comprises first and second blocks for respectively engaging the first and second longitudinal ends of the opening in the blade.

4. A tool arming cartridge as claimed in claim 3, wherein the first block comprises a first cam surface, the first cam surface being arranged such that the first block is disengaged from the first longitudinal end of the opening in the blade when the blade supporting portion of the tool handle is inserted into the housing.

5. A tool arming cartridge as claimed in claim 4, wherein the housing comprises a ramp adjacent to the open longitudinal end and the ramp guides the blade supporting portion of the tool handle towards the first cam surface.

6. A tool arming cartridge as claimed in claim 3, wherein the second block comprises a second cam surface, the second cam surface being arranged such that the second block is disengaged from the second longitudinal end of the opening in the blade when the blade supporting portion of the tool handle is removed from the housing.

7. A tool arming cartridge as claimed in claim 1, wherein the housing defines a longitudinal end opposite the open longitudinal end and the blade engaging means engages the opening in the blade in such a manner that the blade is prevented from moving toward either longitudinal end.

8. A tool arming cartridge as claimed in claim 1, wherein the housing defines a closed longitudinal end opposite the open longitudinal end and the blade engaging means engages the blade in such a manner that the blade is secured in spaced relation to the closed longitudinal end.

9. A tool arming cartridge as claimed in claim 1, wherein the opening in the blade defines first and second longitudinal ends, the housing comprises a wall member and the blade engaging means comprises at least one block cantilevered to the wall member for engaging at least one of the longitudinal ends of the opening.

10. A tool arming cartridge as claimed in claim 9, wherein the blade engaging means comprises first and second blocks respectively cantilevered to the first wall member for respectively engaging the first and second longitudinal ends of the opening in the blade.

11. A tool arming cartridge as claimed in claim 9, wherein the wall member defines a first wall member and the housing further comprises a second wall member and attachment means for attaching the first wall member to the second wall member to form the housing.

12. A tool arming device for holding blades and facilitating mounting of the blades onto a tool handle having a blade supporting portion, each blade defining an opening adapted to receive the blade supporting portion, the tool arming device comprising:

at least two cartridges, each of the cartridges defining an interior and an open longitudinal end, and each of the cartridges including blade engaging means, associated with the interior and movable between an engaged position and a disengaged position, for releasably engaging the opening in the blade, and biasing means for biasing the blade engaging means into the engaged position; and connecting means, associated with at least one of the cartridges, for connecting the cartridges to one another;

wherein the blade engaging means are reoriented from the engaged position to the disengaged position when the blade supporting portion of the tool handle is inserted into the open longitudinal end of the housing.

13. A tool arming cartridge for use with a tool handle having a blade supporting portion, the tool arming cartridge comprising:

a blade defining an opening adapted to receive the blade supporting portion;

a housing defining an interior and an open longitudinal end;

blade engaging means, associated with the interior of the housing and movable between an engaged position and a disengaged position, for releasably engaging the opening in the blade; and biasing means for biasing the blade engaging means into the engaged position;

wherein the blade engaging means are reoriented from the engaged position to the disengaged position when the blade supporting portion of the tool handle is inserted into the open longitudinal end of the housing.

* * * * *